United States Patent [19]

Dobinson et al.

[11] Patent Number: 5,280,069

[45] Date of Patent: Jan. 18, 1994

[54] N-GLYCIDYL COMPOUND

[75] Inventors: Bryan Dobinson, Duxford; Michael R. Thoseby, Cambridge, both of England

[73] Assignee: Ciba-Geigy Corporation, Ardsley, N.Y.

[21] Appl. No.: 693,874

[22] Filed: Apr. 30, 1991

[30] Foreign Application Priority Data

May 5, 1990 [GB] United Kingdom ............... 9010221

[51] Int. Cl.⁵ ............... C07D 303/36; C08G 59/50
[52] U.S. Cl. .................... 525/109; 549/552; 549/514; 528/341; 528/363; 528/407; 528/408; 528/418
[58] Field of Search ............... 525/109; 528/341, 363, 528/407, 408, 418; 549/552

[56] References Cited

U.S. PATENT DOCUMENTS

| | | | |
|---|---|---|---|
| 2,921,037 | 1/1960 | Andres et al. | 260/2 |
| 3,691,133 | 9/1972 | Sara | 528/90 |
| 4,305,861 | 12/1981 | Marx et al. | 528/119 |
| 4,540,769 | 9/1985 | Dobinson et al. | 528/99 |
| 4,560,739 | 12/1985 | Zahir | 528/99 |
| 4,916,202 | 4/1990 | Batler et al. | 528/99 |
| 4,957,995 | 9/1990 | Saito et al. | 528/99 |

FOREIGN PATENT DOCUMENTS

| | | |
|---|---|---|
| 148117 | 7/1985 | European Pat. Off. |
| 874750 | 8/1961 | United Kingdom |
| 2111977 | 7/1983 | United Kingdom |

OTHER PUBLICATIONS

Japanese Patent 247,417, Publication Date Oct. 1989, English Language Translation.
Derwent Abst 89-330117/45 (JO 1247-417A).

Primary Examiner—Frederick Krass
Attorney, Agent, or Firm—JoAnn Villamizar; William A. Teoli, Jr.

[57] ABSTRACT

The new compound N,N,N'N'-tetraglycidyl-3,3'-diethyl-4,4'-diaminodiphenylmethane and curable resin compositions containing it.

18 Claims, No Drawings

N-GLYCIDYL COMPOUND

The present invention relates to N-glycidyl compound.

Epoxide resins are widely used in industry as adhesives, coatings, castings, insulants and in reinforced composites. A variety of chemically distinct epoxide resins are available for this purpose. Such resins are commonly glycidyl ethers or esters derived from epichlorohydrin and a bisphenol or a dicarboxylic acid. Where good performance at high temperature is required, however, as is the case in the aerospace industry, the use of epoxide resins having glycidyl groups attached to aromatic amino groups is often preferred. Such materials are prepared by reaction of the aromatic amine with about 0.8-10 equivalents, per amino hydrogen atom, of epichlorohydrin; followed by conventional dehydrochlorination, using an alkali. This reaction may be carried out in the presence of an acid catalyst in the manner described, e.g. in British Patent Specification No. 2111977.

In European Patent Specification 143075 a process for the production of improved N-glycidyl amines having a higher epoxide content and a lower viscosity than previously-known materials, is described. The improved N-glycidyl amines of EP 143075 are produced by effecting the reaction of aromatic amines with at least 0.7 equivalent, preferably 0.8 to 1.5 equivalents, per amino equivalent of the aromatic amine of epichlorohydrin in the presence of a di- or higher-valent metal salt of a) nitric acid or perchloric acid or b) a carboxylic or sulphonic acid substituted by fluorine, chlorine or bromine on the carbon atom alpha to the carboxylic or sulphonic acid group.

We have now found that by reacting a specific aromatic amine, namely, 3,3'-diethyl-4,4'-diaminodiphenylmethane, with epichlorohydrin, a new N-glycidyl amine is produced, viz. N,N,N'N'-tetraglycidyl-3,3'-diethyl-4,4'-diaminodiphenyl methane having improved properties, especially improved viscosity properties relative to the generality of N-glycidyl amines produced by the process of the EP 143075.

Accordingly, the present invention provides the compound N,N,N'N'-tetraglycidyl-3,3'-diethyl-4,4'-diaminodiphenyl methane, having the formula (I):

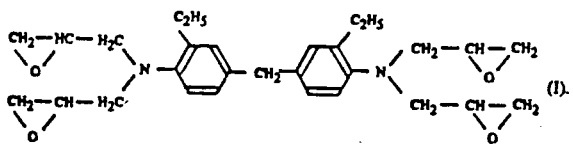

While generic structures, embracing broadly the compound of formula (I) and even describing reaction mixtures containing some proportion of the compound of formula I have been disclosed, e.g. in EP 143075 and in JP-074552, the pure specific compound of formula I is believed to be novel.

The compound of formula I may be produced, as indicated hereinbefore, by reacting 3,3'-diethyl-4,4'-diaminodiphenyl methane with epichlorohydrin, preferably in the presence of a catalyst and, most preferably, using the catalysts described in EP 143075.

Thus, specific preferred salts for use as catalysts in the production of the compound of formula I are magnesium perchlorate, calcium perchlorate, zinc perchlorate, nickel perchlorate, magnesium nitrate, manganese nitrate, lanthanum nitrate, ytterbium nitrate, uranyl nitrate, magnesium trifluoroacetate, manganese trifluoroacetate, nickel trifluoroacetate, vanadyl trifluoroacetate, magnesium trifluoromethanesulphonate, colbalt trifluoromethanesulphonate, lanthanum trifluoroacetate, lanthanum trifluoromethane sulphonate, magnesium trichloroacetate, magnesium-2,2-dichloropropionate and magnesium tribromoacetate.

The amount of salt present in the reaction between 3,3'-diethyl-4,4'-diaminodiphenyl methane and epichlorohydrin is generally within the range of from 0.1 to 10 parts, especially 0.4 to 2 parts, per 100 parts of 3,3'-diethyl-4,4'-diaminodiphenyl methane.

The preferred mode of incorporating the catalyst into the reaction mixture comprising 3,3'-diethyl-4,4'-diaminodiphenyl methane and epichlorohydrin, is by adding the catalyst dissolved in an inert solvent. Examples of inert solvents include 2-methoxyethanol, isodecanol, ethyleneglycol, diethyleneglycol, N-methylpyrrolidone, gamma butyrolactone, benzyl alcohol, dibutyl phthalate, butane-1,4-diol, ethyl methyl ketone, benzene and toluene.

The reaction is usually effected at an elevated temperature, preferably at a temperature within the range of from 50° C. to 100° C. When the reaction between 3,3'-diethyl-4,4'-diaminodiphenyl methane and epichlorohydrin is complete, usually within 1 to 12 hours, the dehydrochlorination is effected in conventional manner, e.g. by adding sodium hydroxide or potassium hydroxide, optionally with the addition, as phase transfer catalyst, of a quaternary ammonium halide such as benzyltrimethyl ammonium chloride. After heating, e.g. for 2 to 10 hours at 50°-100° C., the reaction mixture may be washed with water, and the organic phase separated to produce the desired N-glycidyl amine of formula I. The compound of formula I may be purified by conventional methods, if desired, prior to use e.g. in curable epoxy resin compositions.

The present invention also provides a curable resin composition comprising a) the compound of formula I, as epoxide resin component;

b) a hardener; and, optionally, c) a curing accelerator.

The hardener component b) is preferably a nitrogen-containing compound which remains inert towards the epoxy compound of formula I below a certain "threshold" temperature, which is usually at least 80° C. and is preferably at least 100° C., but which reacts rapidly to effect curing once that threshold temperature has been exceeded. Such materials are well known in this art and are commercially available. They include boron trichloride/amine and boron trifluoride/amine complexes; dicyandiamide; melamine; diallylmelamine; guanamines such as acetoguanamine and benzoguanamine; aminotriazoles such as 3-amino-1,2,4-triazole; hydrazides such as adipic-, stearic- and isophthalic hydrazides; semicarbazide; cyanoacetamide; and aromatic polyamines such as diaminodiphenyl sulphones. The hardener component b) may also be acidic in nature, examples of which are polyphenols, polycarboxylic acids and, especially di- and polycarboxylic acid anhydrides, most particularly hexhydrophthalic anhydride or methyl tetrahydrophthalic anhydride.

The curable resin composition according to the present invention generally contains 1 to 60 wt. %, preferably 5 to 50 wt. % of the hardener component b), based on the amount of epoxide resin component a).

The optional curing accelerator, component c) of the compositions of the present invention, are again known materials in this art and the selection of the accelerator will depend on the type and reactivity of the hardener component b). Examples of such accelerators include solid solutions of a nitrogen base having a boiling point above 130° C. and a phenolic polymer which is an addition polymer of a phenol bearing an unsaturated substituent, as described in European Patent Specification 0200678; and a reaction product of a nitrogen base and a halogen-substituted monomeric phenol, as described in European Patent Specification No. 0240459. Further examples of curing accelerators incude; latent Lewis acid complexes such as the $BF_3$-ethylamine; latent bases such as N,N-dimethylureas and $BCl_3$-amine complexes; and basic accelerators such as tertiary amines.

The amount of the optional accelerator, component c), is not critical and may range from 0 to 15, preferably from 0 to 10 wt. %, based on the weight of component a).

The new compositions according to the present invention may also contain one or more of suitable plasticizers such as dibutyl phthalate or dioctyl phthalate; inert diluents e.g. tars and bitumen; and so-called reactive diluents, especially monoepoxides e.g. n-butyl glycidyl ether, iso-octyl glycidyl ether, phenyl glycidyl ether, cresyl glycidyl ether, glycidyl esters of mixed tertiary, aliphatic monocarboxylic acids, glycidyl acrylate and glycidyl methacrylate. The compositions of the invention may also contain other polyglycidyl resins such as glycidyl derivatives of polyphenols, polyalcohols, and polycarboxylic acids. The compositions may also contain additives such as fillers; reinforcing materials; polymeric toughening agents such as polyether sulphones, phenoxy resins and butadiene-acrylonitrile rubbers; colouring matter; flow control agents; flame retardants; and mould lubricants.

Suitable extenders, fillers and reinforcing materials are, e.g., glass fibres, carbon fibres, fibres of aromatic polyamides, ballotini, mica, quartz flour, calcium carbonate, cellulose, kaolin, wollastonite, colloidal silica having a large specific surface area, powdered poly(vinyl chloride) and powdered polyolefin hydrocarbons such as polyethylene and polypropylene.

The compositions of the present invention are useful as laminating resins, impregnating and casting resins, powder coatings, moulding compositions, putties and sealing compounds, potting and insulating compounds for the electrical industry, but especially as casting resins, laminating resins, and impregnating resins.

The compositions of the invention are conveniently cured by heating them at a temperature in the range of from 100° C. to 200° C., especially 150° C. to 180° C. Usually, heating for 60 to 180 minutes suffices to achieve curing but post-curing at higher temperatures may be necessary to achieve optimum properties.

Relative to conventional resins, the new compound of formula I shows a substantial reduction in viscosity, with subsequent improved ease of processing, and substantial improvement in shelf life with 4,4'-diaminodiphenyl sulphone, with no significant reduction in Tg.

The following Examples further illustrate the present invention.

EXAMPLE 1

3,3'-Diethyl-4,4'-diaminodiphenylmethane (100 g.), toluene (150 g.) and 50% lanthanum nitrate in 2-methoxyethanol (2 g.) are stirred and heated to 60° C. under a vacuum of 120 mm. Epichlorohydrin (158.6 g.) is then added, in portions, over 1 hour, the temperature being maintained at 60° C. by means of vacuum reflux. At the end of this addition, the reaction mixture is maintained at 60° C. for 15 mins. and then vacuum is broken. A further portion of catalyst solution (2 g.) is added and the temperature raised to 80° C. and held at 80° C. for 9 hours. The temperature is reduced to 60° C., and 50% aqueous benzyltrimethylammonium chloride (1.5 g.) added and the apparatus set up for vacuum azeotrope. 50% aqueous sodium hydroxide (151 g.) is then added over 3 hours, water being azeotroped out under vacuum (100 mm). At the end of the addition, azeotrope is continued for a further 90 minutes. Water (300 ml.) is then added with vigorous stirring. The aqueous layer is discarded and the organic layer washed with 10% aqueous sodium dihydrogen phosphate (200 ml.), and evaporated in vacuo on a rotary evaporator. The residue is redissolved in toluene (250 ml.), filtered and evaporated in vacuo to give a product having an epoxide content of 7.89 mol./kg. (94.9% of the theoretical value), a viscosity at 25° C. of 7.1 Pas, and a monomer content (measured by HPLC) of 92.9%.

EXAMPLE 2

A sample of resin from Example 1 (10 g.), 4,4'-diaminodiphenylsulphone (4.9 g.) and Aerosil R 805 (0.3 g.) are milled together in a triple roll mill. A sample of this mix is then stored at 60° C. and periodically tested to check whether the mixture is of a sufficiently low viscosity to be still usable. After 73 days the viscosity of the mix has exceeded usable limits. Another sample of the mix is cured for 3 hours at 175° C. followed by a post-cure of 2 hours at 205° C. The cured sample is found to have a $T_g$ of 261° C.

A similar composition containing the glycidyl derivative of 4,4'-diaminodiphenylmethane, which itself has a viscosity at 25° C. of 100.7 Pas, has a shelf life of 10 days at 60° C. and a Tg of 260° C.

We claim:
1. A curable resin composition comprising:
   a) an epoxide resin component consisting essentially of the pure specific compound N,N,N',N'-tetraglycidyl-3,3'-diethyl-4,4'-diaminophenylmethane;
   b) a hardener; and optionally,
   c) a curing accelerator.
2. A composition according to claim 1, in which component b) is a nitrogen-containing compound which remains inert towards N,N,N',N'-tetraglycidyl-3,3'-diethyl-4,4'-diaminodiphenylmethane below a temperature of at least 80° C.
3. A composition according to claim 2 in which component b) remains inert towards N,N,N',N'-tetraglycidyl-3,3'-diethyl-4,4'-diaminodiphenylmethane below a temperature of at least 100° C.
4. A composition according to claim 1 in which component b) is a boron trichloride/amine or boron trifluoride/amine complex; dicyandiamide; melamine; diallymelamine; a guanamine; an aminotriazole; a hydrazide; semicarbazide; cyanoacetamide; or an aromatic polyamine.
5. A composition according to claim 4 in which the guanamine is acetoguanamine or benzoguanamine; the aminotriazole is 3-amino-1,2,4-triazole; the hydrazide is adipic-, stearic- or isophthalic hydrazide; and the aromatic polyamine is diaminodiphenylsulphone.

6. A composition according to claim 1 in which component b) is a polycarboxylic acid or a polycarboxylic acid anhydride.

7. A composition according to claim 6 in which the polycarboxylic acid anhydride is hexahydrophthalic anhydride or methyl tetrahydrophthalic anhydride.

8. A composition according to claim 1 in which the curable resin composition contains 1 to 60 wt. %, of hardener component b) based on the amount of component a).

9. A composition according to claim 8 in which the curable resin composition contains 5 to 50 wt. % of hardener component b), based on the amount of component a).

10. A composition according to claim 1 in which the curable resin composition contains 0 to 15 wt. % of component c), based on the weight of component a).

11. A composition according to claim 10 in which the curable resin composition contains 0 to 10 wt. % of component c), based on the weight of component a).

12. A composition according to claim 1 in which one or more of plasticizer, an inert diluent or a reactive diluent are also present.

13. A composition according to claim 1 in which one or more of a filler, a reinforcing material, a polymeric toughening agent, a colouring agent, a flow-control agent, a flame retardant or a mould lubricant is also present.

14. A laminating-, impregnating- or casting resin, a powder coating, a moulding composition, a putty or sealing compound, or a potting or electrically insulating compound comprising the composition of claim 1.

15. A composition according to claim 1, in which the curing accelerator is present and is a latent Lewis acid complex, a base or a latent base.

16. A composition according to claim 15, in which the curing accelerator is a $BF_3$-amine complex; a substituted urea; or a tertiary amine or a complex thereof with $BCl_3$.

17. A composition according to claim 16, in which the $BF_3$-amine complex is a $BF_3$-ethylamine complex and the substituted urea is monuron or chlortoluron.

18. A composition according to claim 15, in which the curing accelerator is a solid solution of a nitrogen base having a boiling point above 130° C. and a phenolic polymer which is an addition polymer of a phenol bearing an unsaturated substituent; or a reaction product of a nitrogen base and a halogen-substituted monomeric phenol.

* * * * *